(12) United States Patent
Lippard et al.

(10) Patent No.: US 8,574,914 B2
(45) Date of Patent: Nov. 5, 2013

(54) METHODS FOR MOBILE ZINC MEASUREMENT

(75) Inventors: Stephen J. Lippard, Cambridge, MA (US); Xiao-an Zhang, Toronto (CA); Zdravka Medarova, Methuen, MA (US); Anna Moore, Dracut, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/390,241

(22) PCT Filed: Aug. 12, 2010

(86) PCT No.: PCT/US2010/045245
§ 371 (c)(1),
(2), (4) Date: Apr. 27, 2012

(87) PCT Pub. No.: WO2011/019864
PCT Pub. Date: Feb. 17, 2011

(65) Prior Publication Data
US 2012/0270262 A1 Oct. 25, 2012

Related U.S. Application Data

(60) Provisional application No. 61/233,179, filed on Aug. 12, 2009.

(51) Int. Cl.
*G01N 33/20* (2006.01)
(52) U.S. Cl.
USPC .......................................................... 436/81
(58) Field of Classification Search
USPC .......................................................... 436/81
See application file for complete search history.

(56) References Cited

U.S. PATENT DOCUMENTS

| 7,160,732 | B2 * | 1/2007 | Lippard et al. | 436/172 |
|---|---|---|---|---|
| 2004/0224420 | A1 * | 11/2004 | Lippard et al. | 436/74 |
| 2004/0229300 | A1 * | 11/2004 | Frederickson | 435/7.23 |
| 2005/0142067 | A1 * | 6/2005 | Frederickson et al. | 424/9.6 |
| 2007/0054406 | A1 * | 3/2007 | Frederickson | 436/81 |

FOREIGN PATENT DOCUMENTS

WO 2004094652 A2 11/2004

OTHER PUBLICATIONS

Costello L. et al. Prostatic Fluid Electrolyte Composition for the Screening of Prostate Cancer. Prostate Cancer and Prostatic Diseases 12:17-24, Jul. 1, 2008.*
Louie M. et al. Novel Luminescent Tricarbonylrhenium Polypyridine Tyramine Derived Dipicolylamine Complexes as Sensors . . . Organometallics 28:4297-4307, 2009.*
Frederickson C. et al. The Neurobiology of Zinc in Health and Disease Nature Reviews Neuroscience. Published online May 13, 2005, pp. 1-14.*
Zhang, X., et al., "New Strategy for Quantifying Biological Zinc by a Modified Zinpyr Fluorescence Sensor," J. Am. Chem. Soc., Oct. 31, 2008, vol. 130, pp. 15788-15789.

* cited by examiner

*Primary Examiner* — Ralph Gitomer
(74) *Attorney, Agent, or Firm* — Nixon Peabody LLP; David S. Resnick; Leena H. Karttunen Contarino

(57) ABSTRACT

This invention relates to a method for using a zinc sensor compound to detect a disease associated with the disruption of zinc homeostasis, such as prostate cancer. The zinc sensor compound comprises an optical reporter having two or more recognition units where each of the recognition units is capable of associating with at least one zinc ion.

21 Claims, 5 Drawing Sheets

FL: OPTICAL REPORTER GROUP
X₁ AND X₂: ANALYTE BINDING UNITS

METHODS FOR MOBILE ZINC MEASUREMENT

GOVERNMENT SUPPORT

This invention was made with government support under Grant No. R01 GM065519 awarded by the National Institutes of Health. The government has certain rights in this invention.

CROSS-REFERENCE TO RELATED APPLICATIONS

This application is a 35 U.S.C. §371 National Phase Entry Application of International Application No. PCT/US2010/045245 filed on Aug. 12, 2010, which designated the United States and which claims benefit under 35 U.S.C. §119(e) of U.S. Provisional Application No. 61/233,179, filed Aug. 12, 2009, the content of which is incorporated herein by reference in its entirety.

FIELD OF THE INVENTION

The invention relates to methods for using a zinc sensor compound to detect a disease associated with the disruption of zinc homeostasis, such as prostate cancer.

BACKGROUND OF THE INVENTION

As a ubiquitous and indispensable micronutrient in the human body, zinc ions ($Zn^{2+}$) are present in every mammalian cell and play a pivotal role in a broad range of fundamental physiological functions. The forms of biological zinc can be divided into two categories: tightly bound zinc, which serves as structural and catalytic components of metalloprotein scaffolds, and mobile zinc, which exists in certain mammalian organs, including the brain, retina, pancreas, and prostate, and functions as an essential molecular signaling agent. The homeostasis of $Zn^{2+}$, the process that controls a balanced level of the ion in all tissues, is strictly regulated under physiological conditions. When this process breaks down, as in diseases such as prostate cancer, there is a significant disruption of the proper, physiologically controlled levels of extra- and intracellular mobile $[Zn^{2+}]$. The ability to measure and accurately quantify mobile zinc ions in these organs offers a potentially powerful method for early diagnosis of such zinc-related diseases, such as prostate cancer.

The healthy prostate contains high concentrations of mobile zinc, which decrease significantly during the development of prostate cancer, even at an early stage. Thus reduced zinc levels are a biochemical hallmark of prostate cancer development. The importance of diagnosing prostate cancer early is indisputable. Prostate cancer is the second leading cause of cancer death in men, exceeded only by lung cancer. According to the American Cancer Society, it accounts for about 13 percent of male cancer-related deaths. In its early stages, when it is still curable, prostate cancer causes no symptoms. Notably, the 5-year disease-specific survival rates for localized cancer are 100%. By contrast, metastatic prostate cancer is not curable and has an overall 5-year survival of just 33%. Life expectancy can be as low as 13 months, even in the presence of androgen-deprivation therapy. See Mannuel, H. D.; Hussain, A. *Clin. Genitourin. Cancer* 2006, 5, 43-9. Consequently, the ability to diagnose prostate cancer early, before it has spread beyond the confines of the organ, could offer the only possibility of a cure to patients at risk for aggressive disease. Indeed, with the advent of routine testing for serum prostate specific antigen (PSA), the 5-year cancer-specific survival rates have increased from approximately 70% in the early 1980s to over 90% just a decade later. The significance of early diagnosis and intervention is especially pronounced when considering younger men with a longer life expectancy. A recent study found that, in men under the age of 50, disease-specific survival at 16 years was 73%, whereas of the men treated with radical prostatectomy, 94% were alive at 21 years of observation.

There is thus an ongoing need for methods of treating and diagnosing prostate cancer and benign prostatic hyperplasia.

SUMMARY OF THE INVENTION

This invention relates to a method for using a zinc sensor compound to detect a disease associated with the disruption of zinc homeostasis. The zinc sensor compound comprises an optical reporter having two or more recognition units where each of the recognition units is capable of associating with at least one zinc ion.

The invention also relates to a method of quantifying zinc using a zinc sensor compound. The zinc sensor compound comprises an optical reporter having two or more recognition units where each of the recognition units is capable of associating with at least one zinc ion. The method includes the steps of exposing a zinc sensor compound to a sample; measuring at least one property of the optical reporter of the zinc sensor compound after the optical reporter has been exposed to the sample; and determining the quantity of zinc in the sample based on the measurement or measurements.

The invention also relates to a method of diagnosing a patient as having a disease associated with the disruption of zinc homeostasis. The method comprising quantifying zinc using a zinc sensor compound. The zinc sensor compound comprises an optical reporter having two or more recognition units where each of the recognition units is capable of associating with at least one zinc ion. The method includes the steps of exposing a zinc sensor compound to a sample; measuring at least one property of the optical reporter of the zinc sensor compound after the optical reporter has been exposed to the sample; determining the quantity of zinc in the sample based on the measurement or measurements; and diagnosing the patient, at least in part, on the basis of the determination.

DETAILED DESCRIPTION

Figure 1:
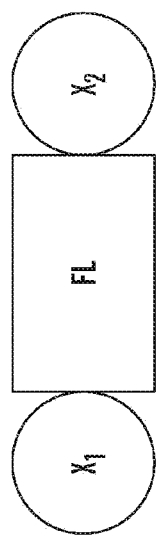
FIG. 1 depicts the general molecular construction in the invention involving attachment of two or more selective analytes (more specifically, but not limited to, $Zn^2$) at recognition/binding units ($X_1$ and $X_2$) in close proximity to a reporter, or more specifically, an optical reporter such as a fluorophore (FL).

One of the purposes of the invention is to provide a means to detect, quantify, and image biological mobile zinc as an early marker of prostate cancer and possibly other diseases by a method that uses a family of zinc sensors having a unique biphasic response to the ion, as described below. Zinc sensor compounds are utilized, as a reduction of zinc uptake is a known early event in prostate tumorigenesis and other diseases associated with disruption of zinc homeostasis. This method can be applied to detect zinc associated diseases, in particular (but not limited to), prostate cancer. The invention includes three parts: (1) a family of fluorescent zinc sensors that exhibit a biphasic response upon zinc binding; (2) methods for convenient and accurate zinc quantification using the fluorescence sensors with a biphasic zinc response as in (1); and (3) zinc quantification for diagnostic methods to detect diseases associated with disruption of zinc homeostasis, in particular, but not limited to, prostate cancer.

This invention has several advantages over existing zinc quantification methods, especially with respect to clinical applications. Conventionally, zinc can be quantified by atomic absorption spectroscopy (AAS) or inductively coupled plasma mass spectroscopy (ICP-MS), both of which require expensive and complicated instruments with limited availability and are thus not suitable for wide range and self-test applications. Moreover, these methods measure total zinc, not just mobile zinc that is disease related. The existing fluorescent or colorimetric zinc sensors, can be applied for mobile zinc quantification, in principle; these older generation titration methods, however, lack accuracy and all need calibration curves. They are technically less sensitive and not sufficiently impervious to influences such as pH fluctuations, background fluorescence of the free sensor, interference from other metal species, and the presence of non-zinc components in the solutions, all of which have the potential to perturb the fluorescence or optical signals. The invention provides a more convenient, accurate, robust, sensitive and economical method for zinc quantification, particularly valuable for rapid and reliable diagnosis of mobile zinc associated diseases, such as prostate cancer.

The invention has the tangible potential to supplement current prostate cancer screening tests in order to overcome the considerable level of ambiguity associated with them. In today's clinical practice, digital rectal examination (DRE) and measurements of serum PSA are relied upon to identify patients at risk for prostate cancer, who subsequently undergo an invasive biopsy of the prostate to make a final diagnosis. The DRE test looks for abnormal lumps or firmness in the dorsal wall of the prostate. However, because it is not possible to reach all areas of the prostate, some tumors can go undetected using DRE alone. Additionally, very small prostate cancers are impossible to detect by touch, no matter where they are located, leading to a reduced positive-predictive potential and a low sensitivity.

The Prostate-Specific Antigen (PSA) test measures the amount of PSA in a sample of blood. Although many men with prostate cancer have an elevated PSA concentration (greater than 4.0 ng/mL), a high level does not necessarily mean that there is a cancer. An elevated PSA can be caused by benign prostatic hyperplasia (BPH), a noncancerous enlargement of the prostate, prostate infection (prostatitis), or trauma, to name a few alternatives. These factors reduce the specificity of the method. At the same time, many men with prostate cancer will not have an elevated PSA measurement. In some studies, more than 20 percent of men with prostate cancer had a normal PSA (false-negative test), while up to 40 percent of men without cancer had an abnormal PSA (false-positive test). Overall, only 30 percent of men with abnormal values will have prostate cancer. Refinements in PSA blood testing such as measuring PSA velocity (rate of change over time), PSA density (PSA per volume of prostate tissue), free (unbound) PSA, and complexed (bound to protein) PSA are intended to increase the accuracy of PSA tests, although there is no general agreement about the additional benefits of these refinements.

Consequently, many men will either undergo unnecessary invasive and emotionally taxing treatment or remain undiagnosed. This dilemma has caused many clinicians and scientists to challenge the notion that testing for prostate cancer is warranted, having in mind the slow-growing nature of the malignancy and its reduced influence on the overall survival of older men with a shorter life expectancy.

In disagreement with this philosophy, the recent trials mentioned above affirm the life-saving value of early diagnosis, especially in younger men. Considering that, according to the American Cancer Society, 1 in 35 men in the U.S. will die of prostate cancer, there should be no debate about the need for an effective and reliable diagnostic tool as a facilitator of successful therapy.

It is believed that this invention is superior to existing technologies because it is strictly quantitative (or mostly quantitative) and potentially less ambiguous in its diagnosis of prostate cancer. One of its advantages over screening for serum PSA, for example, lies in the fact that, whereas PSA is elevated in both cancer and BPH, zinc levels are drastically reduced in prostate cancer (from 3 mmol/g dry tissue in the normal peripheral zone to 500 µmoles/g in the malignant peripheral zone), but increased in the case of BPH (4 mmoles/g). See Costello, L. C.; Franklin, R. B. *Prostate Cancer Prostatic Dis.* 2009, 12, 17-24. Therefore, monitoring levels of zinc in the prostate can resolve the differential diagnosis between BPH and cancer, which may be the most challenging elements confounding diagnosis, considering that the majority of men in the high-cancer over 55 age group will develop BPH. A further benefit of the invention in the context of prostate cancer derives from the fact that, as demonstrated below, the method allows the collection of measurements using pro static secretions and therefore presents a noninvasive alternative, unlike biopsy, the DRE, or the measurement of serum PSA. Moreover, the robustness of the measurement is typically greater when using prostatic secretions in particular, because of all prostatic tissues, the prostatic secretions demonstrate the widest margin between the benign and malignant conditions (9 mmoles/g vs. 1 mmole/g). See Costello, L. C.; Franklin, R. B. *Prostate Cancer Prostatic Dis.* 2009, 12, 17-24.

One embodiment of this invention relates to a method for using a zinc sensor compound to detect a disease associated with the disruption of zinc homeostasis. The zinc sensor compound may be any compound that contains an optical reporter having two or more recognition units where each of the recognition units is capable of associating with at least one zinc ion. As used herein, a "zinc ion" is any one of the ions of zinc that are known to exist, including, but not limited to being, $Zn^{2+}$.

The zinc sensor compound is capable of associating with zinc ions that are mobile in a mammal, such as human. The zinc ions may be intracellular or extracellular.

An exemplary zinc sensor compound therefore is any one member of a family of zinc sensors that exhibit biphasic response upon association with one or more zinc ions, such as any one member of that particular family that is described herein, for example. The family of zinc sensors may be fluorescent zinc sensors. However, it is to be understood that the term "zinc sensor compound" is not limited thereto being a member of that family. One of ordinary skill in the art will readily recognize all of the different compositions of matter that can serve as the zinc sensor compound.

The zinc sensor compound may be any compound of formula (I):

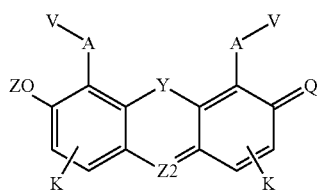
(I)

wherein, independently for each occurrence:

K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, carboxyl (such as —COO⁻), nitro, halogen, sulfhydryl, cyano, hydroxyl, carbamoyl and trifluoromethyl;

A is —CH$_2$—, —C(=O)—, —C(=S)—, —CH$_2$CH$_2$—, —CH$_2$C(=O)—, —CH$_2$C(=S)— or —C(H)=;

Z is hydrogen or any hydroxyl-protecting group;

Q is O, S or Se;

V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphoramidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein the imino group is capable of forming a bidentate chelate;

Y is O, S, Se, NR, or C(CH$_3$)$_2$, wherein R is an alkyl and R and the methyl groups of C(CH$_3$)$_2$ are optionally substituted; and Z2 is N, HOOCCH$_2$CH$_2$C—, HOOC—CH=CH—C—, (2-carboxyphenyl)-C—, or (2-sulfophenyl)-C—, wherein for the (2-carboxyphenyl)-C— and (2-sulfophenyl)-C—, the phenyl moiety is optionally substituted with one or more E, wherein for the HOOCCH$_2$CH$_2$C— and HOOC—CH=CH—C—, the hydrogen atoms of the —CH$_2$—'s and —CH='s moieties are optionally substituted, and wherein E is selected from the group consisting of alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl.

Methods to prepare the above-disclosed zinc sensor may be found in U.S. Pat. No. 7,160,732, herein incorporated by reference in its entirety. Alternative embodiments and subgenera of formula (I) suitable for use with the methods of this invention are also disclosed in U.S. Pat. No. 7,160,732.

In one embodiment, the zinc sensor compound may be any compound having the following formula (II):

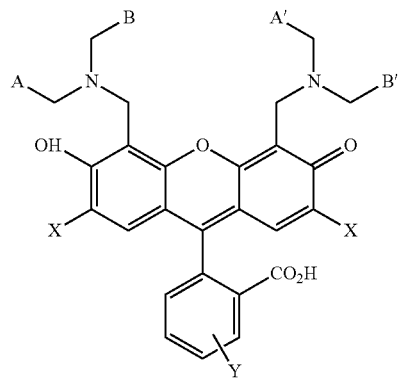
(II)

wherein:

A, A', B, and B' are each independently selected from the group consisting of —COO⁻,

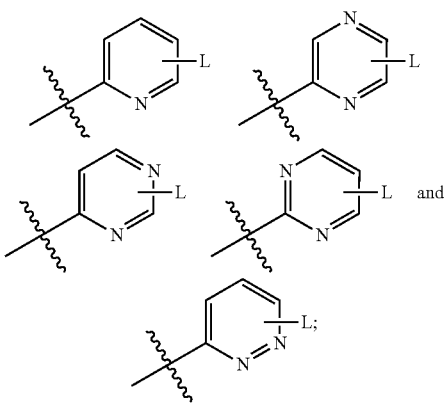

X is H, Cl, or F;
Y is H or —COO⁻; and
L is H, SO$_3$⁻, or COO⁻.

In another embodiment, the zinc sensor compound represents the following compound, also referred to as ZPP1:

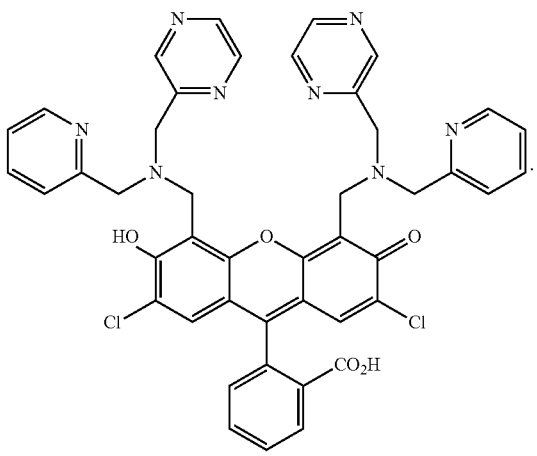 [SMILES: O=C(O)c1ccccc1-c1c2cc(Cl)c(=O)c(CN(Cc3ccccn3)Cc3cnccn3)c-2oc2c(CN(Cc3ccccn3)Cc3cnccn3)c(O)c(Cl)cc12]

The optical reporter can be any component of the zinc sensor compound that has the ability to cause the molecule to provide an optical response, e.g. a component that causes the molecule to be fluorescent. Suitable optical reporters include fluorophore, such as fluorescein or its analogs, such as 2',7'-dichlorofluorescein and 2',7'-difluorofluorescein. In certain instances, the fluorophore is more fluorescent when two or more zinc ions are associated with the recognition units than the fluorophore is when no zinc ions are associated with the recognition units or when one zinc ion is associated with the recognition units.

A "recognition unit" means anything that is capable of associating with at least one zinc ion. Therefore, each one of "zinc sensor," "zinc-binding unit" and "analyte binding unit" is an exemplary "recognition unit," but it is to be understood that "recognition unit" is not limited thereto those examples and therefore is to be construed more broadly than each one of those examples. Other recognition units are contemplated and will be readily recognized by the skilled artisan. Two or more recognition units should be present on the zinc sensor compound. In some embodiments, the compound may contain exactly two recognition units. The recognition units may have the same or different structures. Dipicolylamine and analogs of dipicolylamine, such as 1-(pyrazin-2-yl)-N-(pyridin-2-ylmethyl)methanamine, are examples of suitable recognition units.

For ZPP1, for example, the "recognition unit" is 1-(pyrazin-2-yl)-N-(pyridine-2-ylmethyl)methanamine, and the "optical reporter" is 2',7'-dichlorofluorescein."

A spacer is any chemical compound or element present in the zinc sensor compound that may be used to link two components together. For example, one or more spacers may be present between the optical reporter and the recognition unit. The spacers will not substantively affect the functionality of the optical reporter or the recognition unit, and may be present in the zinc sensor compound for reasons related to the compound (to influence the sterics of the chemical compound) or reasons unrelated to the compound (presence is due to the use of a different base compound that is otherwise preferable).

In certain embodiments, at least one of the recognition units is directly associated with at least one spacer and at least one of those spacers is directly associated with the optical reporter such that at least one of the recognition units is indirectly associated with the optical reporter. In other embodiments, the zinc sensor compound contains exactly two recognition units, a first recognition unit and a second recognition unit. The first recognition unit is directly associated with at least one first spacer and at least one of the first spacers is directly associated with the optical reporter, and the second recognition unit is directly associated with at least one second spacer and at least one of the second spacers is directly associated with the optical reporter such that the first recognition unit and the second recognition unit are indirectly associated with each other through the optical reporter.

The invention also relates to a method of quantifying zinc using a zinc sensor compound. The method includes the steps of exposing a zinc sensor compound to a sample; measuring at least one property (such as fluorescence) of the optical reporter of the zinc sensor compound after the optical reporter has been exposed (such as through titration) to the sample; and determining the quantity (for instance, the concentration) of zinc in the sample based on the measurement or measurements.

The sample may be obtained from a mammal, such as a human. Suitable human samples include intact prostate tissue or cell line, a lysate from a prostate tissue or cell line, and a prostate fluid extract. The prostate fluid extract, for example, may be obtained from an ejaculate, a seminal fluid, a prostatic fluid, or a biopsy sample. Samples may be from humans that have prostate cancer, do not have prostate cancer, or are uncertain whether they have prostate cancer. This last group would often times be providing the sample as a diagnostic.

In one embodiment, at least one of the measurements is measured fluorescence and the measurement is indicative that the human has a normal prostate, that the human has a prostate that is free of cancer, that the human has prostate cancer, or that the human has benign prostatic hyperplasia. The measured fluorescence can be indicative that (a) the human has a prostate that is free of cancer; (b) the human has benign prostatic hyperplasia; or (c) the human has prostate cancer.

The protein and cellular material in the sample is typically removed from the sample prior to the measuring step, with the removal carried out by centrifugation alone or by both sonication and centrifugation.

At least one of the properties measured in the sample can be normalized to a volume of the patient's prostate and to the serum zinc concentration in the patient. The volume of the prostate can be determined by using ultrasound or other means known in the art.

The invention also relates to a method of diagnosing a patient as having a disease associated with the disruption of zinc homeostasis. The method comprises quantifying zinc using a zinc sensor compound. The method includes the steps of exposing a zinc sensor compound to a sample; measuring at least one property of the optical reporter of the zinc sensor compound after the optical reporter has been exposed to the sample; determining the quantity of zinc in the sample based on the measurement or measurements; and diagnosing the patient, at least in part, on the basis of the determination. In this embodiment, the method of quantifying zinc, discussed above, is used in a diagnostic context with a patient having a disease associated with the disruption of zinc homeostasis, such as prostate cancer.

Structure, Method of Preparation, and Properties of Biphasic Zinc Sensors.

As shown in FIG. 1, the general molecular construction in the invention involves attachment of two or more selective analytes (more specifically, but not limited to, $Zn^{2+}$) at recognition/binding units ($X_1$ and $X_2$) in close proximity to a reporter, or more specifically, an optical reporter such as a fluorophore (FL). $X_1$ and $X_2$ can be directly attached to FL, or attached to FL via a molecular spacer. FL can also be or not be involved in binding analyte. $X_1$ and $X_2$ can be identical, but can also be different.

Figure 2:
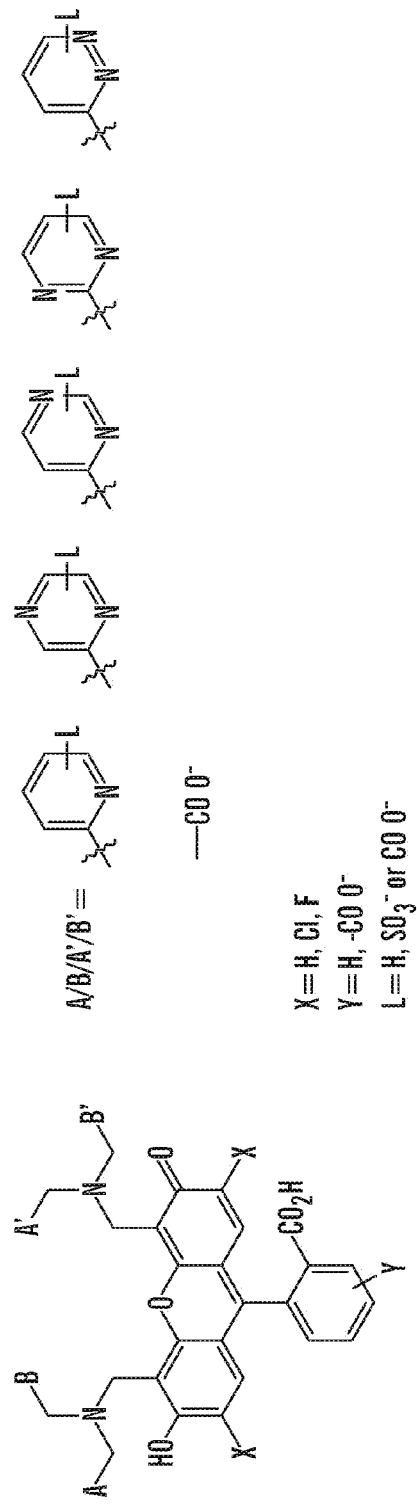
FIG. 2 depicts various zinc sensor compounds.

As shown in FIG. 2, various embodiments of the zinc sensor compound include a fluorescein as a fluorophore, and two nitrogen-rich moieties, as zinc binding units. Suitable nitrogen-rich moieties include dipicolylamine (DPA) or its analogs. DPA is known for binding zinc selectively over $Na^+$, $K^+$, $Mg^{2+}$ and $Ca^{2+}$, the most biologically relevant mobile metal ions species in this context. Other heterocyclic rings that bind zinc in a manner similar to pyridine can substitute one or up to all of the pyridines. Suitable heterocyclic structures include pyrazine, pyrimidine, and pyridazine, as shown in FIG. 2. Other compounds that are zinc-selective and more electron-withdrawing in comparison with pyridine, which can lower the $pK_a$ value of the tertiary nitrogen to avoid its protonation at neutral pH, may also be used. This is a desired property because protonation at the tertiary nitrogen can lead to an increase of fluorescence intensity, similar to the optical response of zinc binding. This $pK_a$ can be further tuned by adding electron-withdrawing groups, X, such as Cl or F, on the fluorescein moiety. Introducing anionic groups, such as carboxylate or sulfate, on zinc binding units or on fluorescein, can prevent the sensor from penetrating the cell membranes, thus rendering it suitable for extracellular applications.

Figure 3:
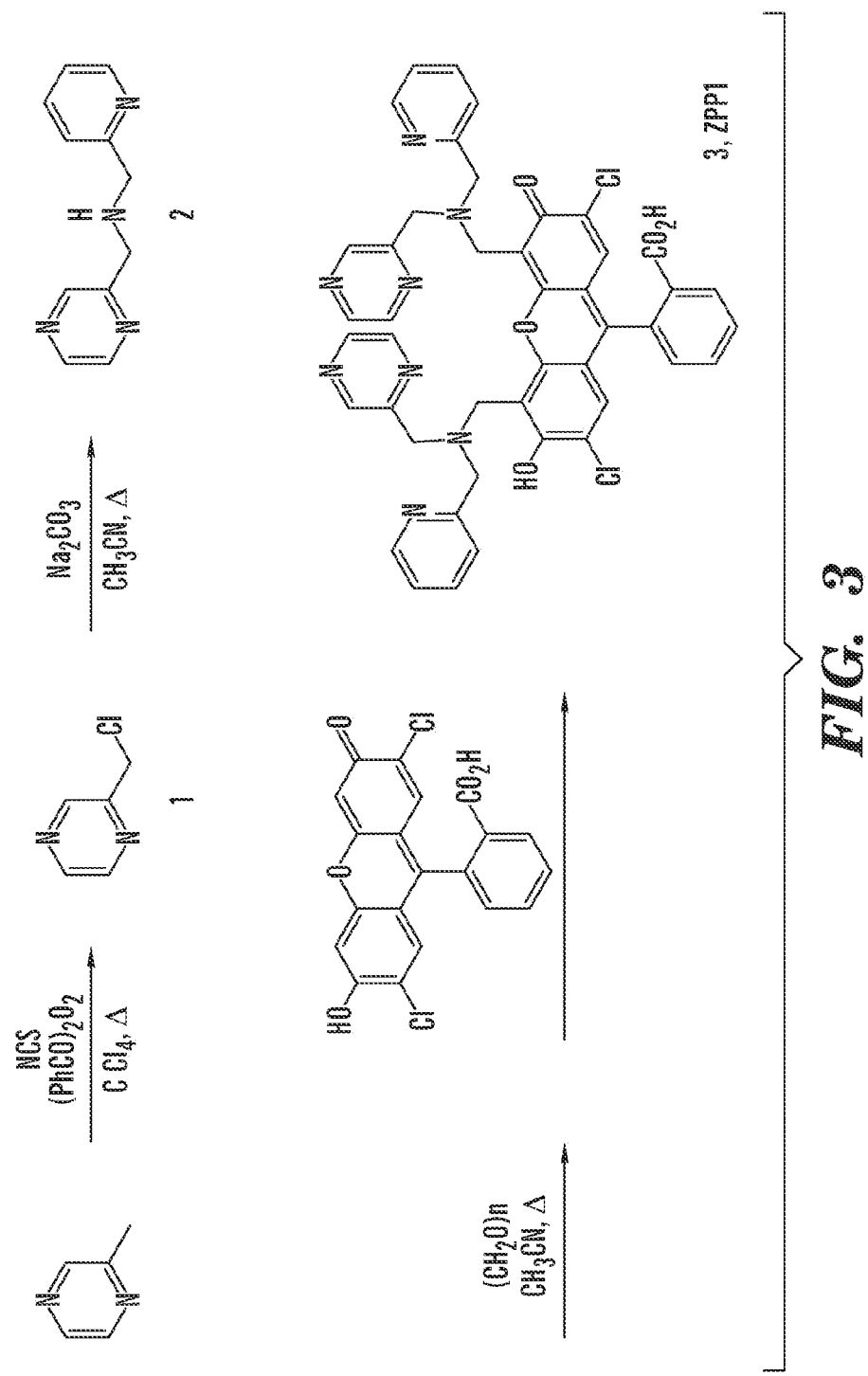
FIG. 3 depicts a synthesis route that may be used to prepare zinc sensor compounds.

This family of zinc sensor compounds can be synthesized using single or separated two-step Mannich reactions involving fluorescein, DPA or an analog, and paraformaldehyde. Other synthetic methods known to those of skill in the art may also be used to prepare the zinc sensor compounds. A specific example of a zinc sensor compound, ZPP1, and its method of preparation, are shown in FIG. 3.

Figure 4:
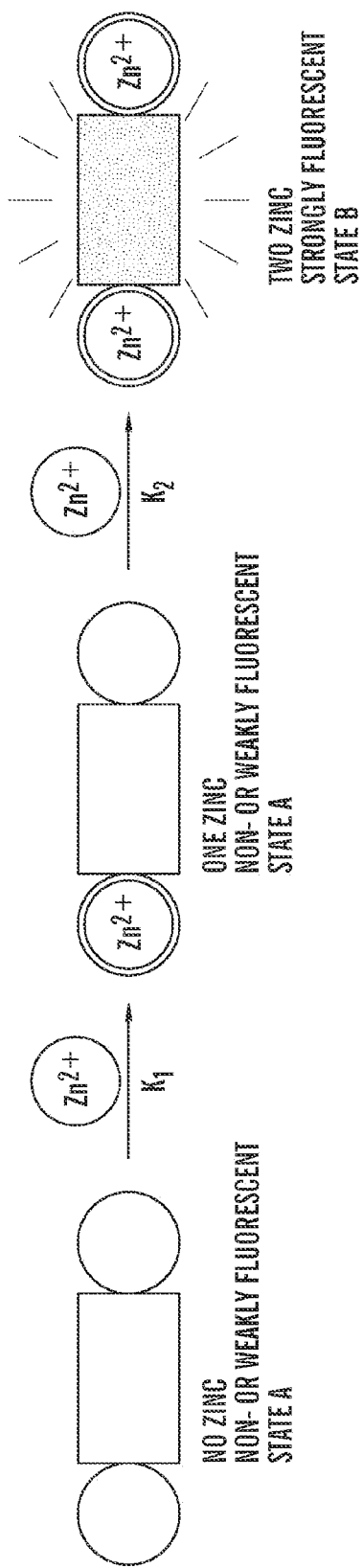
FIG. 4 depicts the biphasic optical response of the zinc sensor compounds towards analyte binding using zinc as an example.

As schematically shown in FIG. 4, the zinc sensor compounds have the following optical properties in response to biphasic binding of two or more equivalents of analyte. The free sensor is in an optical state A, for example (but not limited to), a non- or weakly fluorescent state; binding the first one (or more) equivalent of analyte, does not significantly influence its optical properties (remaining at state A). Binding the next equivalent of analyte, however, leads to a significant change of its optical properties, for example (but not limited to), a significant increase of fluorescent intensity (state B).

In one embodiment, the first binding constant, $K_1$, is significantly higher than $K_2$, the binding constant for the analyte that leads to state B. This property assures, or helps assure, that the predominant species remains at State A, before reaching the stoichiometry of first equivalent of analyte.

Applications

The methods may also be used for clinical and self-test assays and instrumentation for diagnosis of prostate cancer and other diseases demonstrating a disruption of zinc homeostasis.

For instance, the methods can be used in conjunction with an assay in which prostatic secretions are collected at a clinic either through prostatic massage or from an ejaculate or urine. A small volume of the sample can be deposited in a well (e.g. of a 96-well plate) and titrated with a biphasic zinc sensor in parallel with a non-biological buffer. Fluorescence measurements at defined wavelengths can be taken at each step of the titration using a benchtop fluorimeter. The process can be continued until a peak ratio of sample over buffer fluorescence has been passed. Based on the peak ratio, a measurement of sample zinc concentration can be finalized or determined. The process can be performed in a clinical scenario, for instance by a laboratory technician, likely involving a comparison to zinc standards, as well as positive and negative controls to ensure the robustness of the measurement. Set levels that define "normal" and "suspicious" readings can be determined empirically, similarly to serum PSA measurements.

The methods can also be used in conjunction with a self-test kit. In one embodiment, this includes a simplified miniaturized fluorimeter, which only takes readings at the specified excitation and emission wavelengths. The patient can enrich the sample for prostatic fluid from ejaculate (or other biological sample), through brief centrifugation or gravity sedimentation, and then load the fluid into a cell with an eyedropper or a syringe. The instrument can include a container pre-loaded with a zinc sensor, which can be dispensed into the cell containing the sample at pre-set aliquots. The instrument can take readings of the sample and buffer (pre-loaded into a calibration cell of the instrument, in one embodiment) with the addition of each aliquot, record and automatically normalize the readings (in another embodiment), to produce a peak reading and ultimately convert it to a zinc level suitable to be reported to the patient. Since all of the steps of the process are mechanical and involve little or no interpretation, the entire process can be automated.

In view of the above descriptions, one skilled in the art can use the methods of the invention in assays and self-test kits. Various alternative embodiments relating to the assays, self-test kits, and other related devices can also be produced, as appreciated by those of skill in the art. Suitable devices are described in U.S. Provisional Application No. 61/358,530, filed Jun. 25, 2010, entitled "Colorimetric Method and Device for Detecting Analyte Quantities in Fluids and Materials," herein incorporated by reference in its entirety.

The present invention may be defined in any one of the following numbered paragraphs:

Provided is a method for using a zinc sensor compound to detect a disease associated with the disruption of zinc homeostasis, wherein the zinc sensor compound comprises an optical reporter having two or more recognition units, wherein each of the recognition units is capable of associating with at least one zinc ion.

In one aspect of the method, the optical reporter is a fluorophore.

In one aspect of the method, the fluorophore is 2',7'-dichlorofluorescein or 2',7'-difluorofluorescein.

In some aspects of the above-described methods the at least one of the two or more recognition units is 1-(pyrazin-2-yl)-N-(pyridin-2-ylmethyl)methanamine In some aspects of the above-described methods at least two of the recognition units have identical structures.

In some aspects of the above-described methods, each of the recognition units is directly associated with the optical reporter.

In one aspect of the method the zinc sensor compound comprises exactly two recognition units.

In one aspect of the method, none of the recognition units is directly associated with another recognition unit.

In some aspects of the above-described methods, the zinc sensor compound further comprises at least one spacer.

In one aspect of the method, at least one of the recognition units is directly associated with at least one spacer and at least one of those spacers is directly associated with the optical reporter such that at least one of the recognition units is indirectly associated with the optical reporter.

In some aspects of the above-identified methods, the zinc sensor compound comprises exactly two recognition units, a first recognition unit and a second recognition unit, wherein the first recognition unit is directly associated with at least one first spacer and at least one of the first spacers is directly associated with the optical reporter, and the second recognition unit is directly associated with at least one second spacer and at least one of the second spacers is directly associated with the optical reporter, such that the first recognition unit and the second recognition unit are indirectly associated with each other through the optical reporter.

In some aspects of the above-identified methods, at least one of the recognition units has a structure that is selected from the group consisting of —COO⁻,

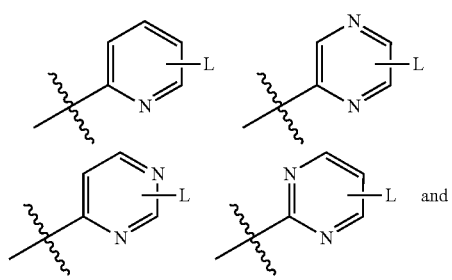

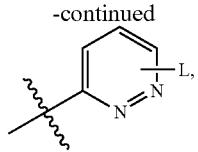

where L is H, $SO_3^-$, or $COO^-$.

In some aspects of the above-identified methods, the zinc sensor compound is a compound of formula (I):

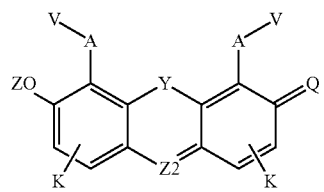

(I)

wherein, independently for each occurrence:

K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, carboxyl, nitro, halogen, sulfhydryl, cyano, hydroxyl, carbamoyl and trifluoromethyl;

A is $—CH_2—$, $—C(=O)—$, $—C(=S)—$, $—CH_2CH_2—$, $—CH_2C(=O)—$, $—CH_2C(=S)—$ or $—C(H)=$;

Z is hydrogen or any hydroxyl-protecting group;

Q is O, S or Se;

V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphonamidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein the imino group is capable of forming a bidentate chelate;

Y is O, S, Se, NR, or $C(CH_3)_2$, wherein R is an alkyl and R and the methyl groups of $C(CH_3)_2$ are optionally substituted; and Z2 is N, $HOOCCH_2CH_2C—$, $HOOC—CH=CH—C—$, (2-carboxyphenyl)-C—, or (2-sulfophenyl)-C—, wherein for the (2-carboxyphenyl)-C— and (2-sulfophenyl)-C—, the phenyl moiety is optionally substituted with one or more E, wherein for the $HOOCCH_2CH_2C—$ and $HOOC—CH=CH—C—$, the hydrogen atoms of the $—CH_2—$'s and $—CH=$'s moieties are optionally substituted, and wherein E is selected from the group consisting of alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl.

In some aspects of the above-identified methods, the zinc sensor compound is a compound formula (II):

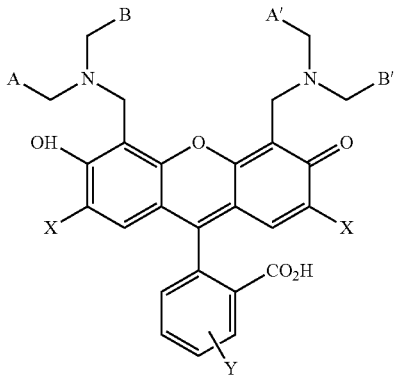

(II)

wherein:

A, A', B, and B' are each independently selected from the group consisting of —COO⁻,

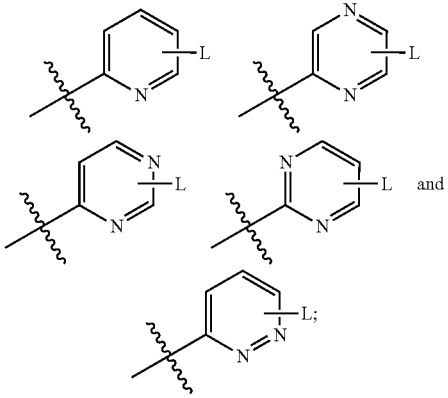

and

X is H, Cl, or F;
Y is H or —COO⁻; and
L is H, $SO_3^-$, or COO⁻.

In some aspects of the above-identified methods, at least one of the recognition units is dipicolylamine.

In some aspects of the above-identified methods, at least one of the recognition units is an analog of dipicolylamine.

In some aspects of the above-identified methods, the fluorophore is more fluorescent when two or more zinc ions are associated with the recognition units than the fluorophore is when no zinc ions are associated with the recognition units or when one zinc ion is associated with the recognition units.

In some aspects of the above-identified methods, the zinc sensor compound is capable of associating with zinc ions that are mobile in a mammal.

In one aspect of the above-identified method, the zinc ions are intracellular.

In one aspect of the above-identified method, the zinc ions are extracellular.

In some aspects of the above-identified methods, the mammal is a human.

In some aspects of the above-identified methods, the disease associated with the disruption of zinc homeostasis is prostate cancer.

Also provided is a method of quantifying zinc, the method comprising:

exposing a zinc sensor compound to a sample, wherein the zinc sensor compound comprises an optical reporter having two or more recognition units wherein each of the recognition units is capable of associating with at least one zinc ion, measuring at least one property of the optical reporter of the zinc sensor compound after the optical reporter has been exposed to the sample, and determining the quantity of zinc in the sample based on the measurement or measurements.

In one aspect of the method, at least one of the properties is fluorescence.

In some aspects of the method, the exposure is titration.

In some aspects of the method, the quantity of the zinc is based on the concentration of the zinc.

In some aspects of the method he sample is obtained from a mammal.

In some aspects of the method, the mammal is a human.

In some aspects of the method, the sample is selected from the group consisting of an intact prostate tissue or cell line, a lysate from a prostate tissue or cell line, a prostate fluid extract, and urine.

In some aspects of the method, the human has prostate cancer.

In one aspect of the method, the sample is a prostate fluid extract and the prostate fluid extract is obtained from an ejaculate, a seminal fluid, a prostatic fluid, a biopsy sample, or a combination thereof.

In some aspects of the method at least one of the measurements is measured fluorescence and the measurement is indicative that the human has a normal prostate, that the human has a prostate that is free of cancer, that the human has prostate cancer, or that the human has benign prostatic hyperplasia.

In one aspect of the method, the measured fluorescence is indicative that the human has a prostate that is free of cancer.

In one aspect of the method, the measured fluorescence is indicative that the human has benign prostatic hyperplasia.

In one aspect of the method, the measured fluorescence is indicative that the human has prostate cancer.

In one aspect of the method, the protein and cellular material in the sample is removed from the sample prior to the measuring step.

In one aspect of the method, the removal is carried out by centrifugation alone or by both sonication and centrifugation.

In one aspect of the method, the sample is obtained from a patient and at least one of the properties measured is normalized to a volume of the patient's prostate and to serum zinc concentration in the patient.

In one aspect of the method, the volume of the prostate is determined by using ultrasound.

Also provided is a method of diagnosing a patient as having a disease associated with the disruption of zinc homeostasis, the method comprising:

exposing a zinc sensor compound to a sample, wherein the zinc sensor compound comprises an optical reporter having two or more recognition units wherein each of the recognition units is capable of associating with at least one zinc ion, measuring at least one property of the optical reporter of the zinc sensor compound after the optical reporter has been exposed to the sample, determining the quantity of zinc in the sample based on the measurement or measurements, and diagnosing the patient, at least in part, on the basis of the determination.

In one aspect of the method, the patient is a mammal.

In one aspect of the method, the mammal is a human.

In one aspect of the method, the diagnosis based at least partially on the method is that the human has a normal prostate, that the human has a prostate that is free of cancer, that the human has prostate cancer, or that the human has benign prostatic hyperplasia.

In one aspect of the method, the diagnosis is that the human has a prostate that is free of cancer.

In one aspect of the method, the diagnosis is that the human has benign prostatic hyperplasia.

In one aspect of the method, the diagnosis is that the human has prostate cancer.

EXAMPLES

Example 1

A specific example of a zinc sensor compound, ZPP1, and its method of preparation, are shown in FIG. 3.

Example 2

Figure 5:
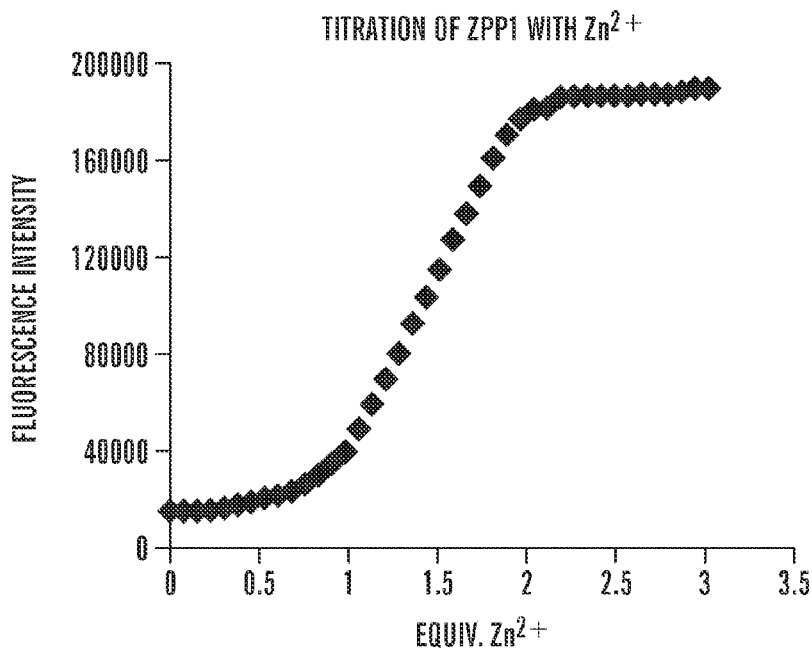
FIG. 5 depicts a chart showing the fluorescent zinc titration for a zinc sensor compound.

As an example, FIG. 5 displays such a fluorescent zinc titration for ZPP1. Addition of up to 1 equiv of zinc to ZPP1 results in only a slight fluorescence increase (remaining at state A); addition of more than 1 equiv leads to a significant, almost linear increase in fluorescence intensity that reaches its maximum near 2 equiv (state B).

Since ZPP1 contains two zinc-binding units, the following stepwise equilibria describe the binding events.

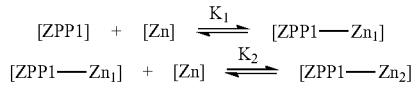

Two apparent binding constants, ($K_{1app}=1.52\times10^{11}$ $M^{-1}$, $K_{2app}=1.02\times10^{8}$ $M^{-1}$) were obtained by fitting the experimental data to the two-step model with high fidelity. In this case, the first step zinc binding constant is significantly (~150 times) higher than that of the second step.

Example 3

Method for Zinc Quantification Using Biphasic Zinc Sensors

Figure 6:
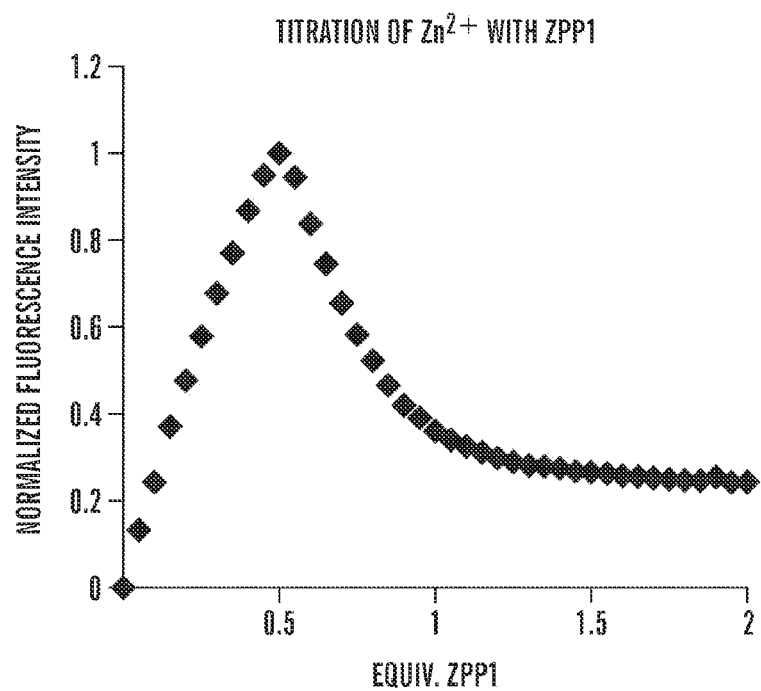
FIG. 6 depicts a chart showing the fluorescence titration of zinc with a zinc sensor compound for zinc quantification.

The biphasic zinc-response properties of the zinc sensor compounds, such as ZPP1, offer a unique opportunity for zinc quantification. By fluorescence titration of a mobile zinc sample with ZPP1, the zinc concentration can be determined from the concentration of sensor giving the maximum, or near maximum, fluorescence response. This was confirmed by an experiment shown in FIG. 6, in which a constant amount of zinc chloride (5 μM) was titrated with ZPP1. There is a distinctive two-step fluorescence response upon addition of increasing amounts of ZPP1. Titration of ZPP1 into a zinc solution first generated the highly fluorescent species ZPP1-$Zn_2$, since excess zinc was available, producing an almost linear increase in fluorescence intensity at the beginning of the titration. When the concentration of ZPP1 reached half the concentration of total zinc ([ZPP1]total=½ [$Zn^{2+}$]$_{total}$), the addition of more ZPP1 shifted the equilibrium to form ZPP1-$Zn_1$, which is only weakly fluorescent. The fluorescence therefore decreased, even though more ZPP1 was added. At the sharp maximum point in the titration curve, the amount of ZPP1 added was equal to half of the total amount of zinc in solution, which allows for an accurate determination of mobile zinc concentration.

Example 4

Figure 7:
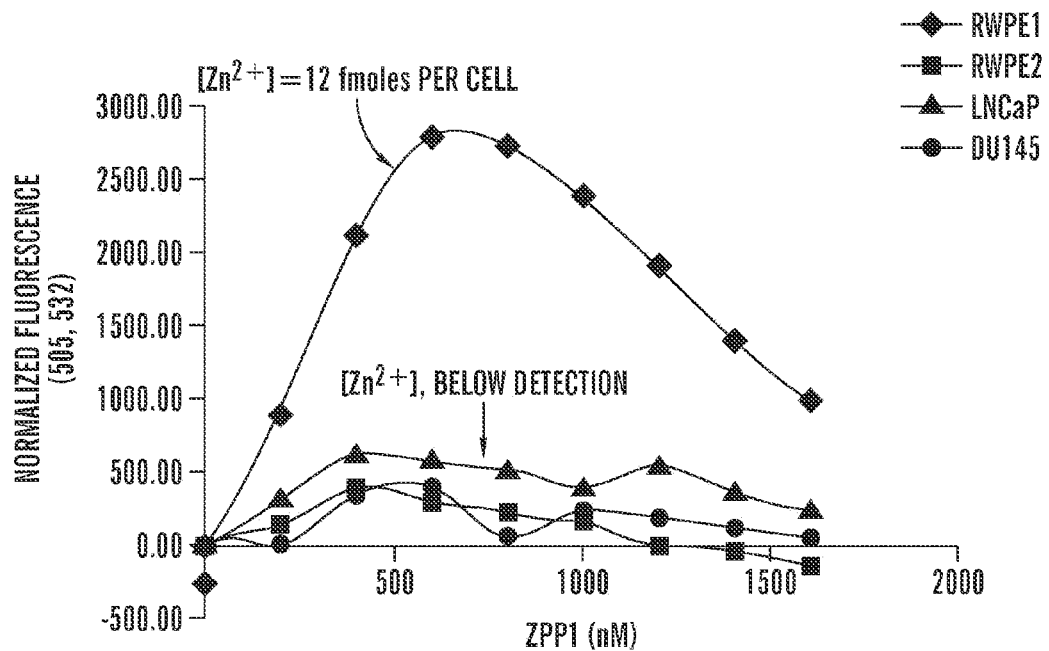
FIG. 7 depicts a chart showing the fluorescence titration of cell lysates with a zinc sensor compound for zinc quantification.

Application of Zinc Quantification Method for Detecting Prostate Cancer Using Biphasic Zinc Sensor The biphasic zinc-response properties of the zinc sensor compounds, such as ZPP1, were successfully applied in a biological context for the determination of zinc concentration in (a) non-transformed and transformed prostate cell lines, and (b) prostatic fluid extracts from healthy mice and transgenic mice with prostate cancer (transgenic adenocarcinoma of the mouse prostate, TRAMP). Fluorescence titrations were performed of cell lysates (a) or prostatic fluid extracts (b) with ZPP1 and determined the zinc concentration from the concentration of sensor giving the maximum fluorescence response, as described in Example 3. Whereas the noncancerous prostate cell line (RWPE1) demonstrated a clear peak corresponding to a zinc level of 12 fmols per cell, none of the prostate carcinoma cell lines revealed measurable zinc levels. See FIG. 7. Since these cell lines represent a broad spectrum, from virally transformed (RWPE2) to androgen-dependent (LNCaP) and androgen-independent (DU145) prostate cancer, these results suggest a broad diagnostic applicability of the approach.

Example 5

Figure 8:
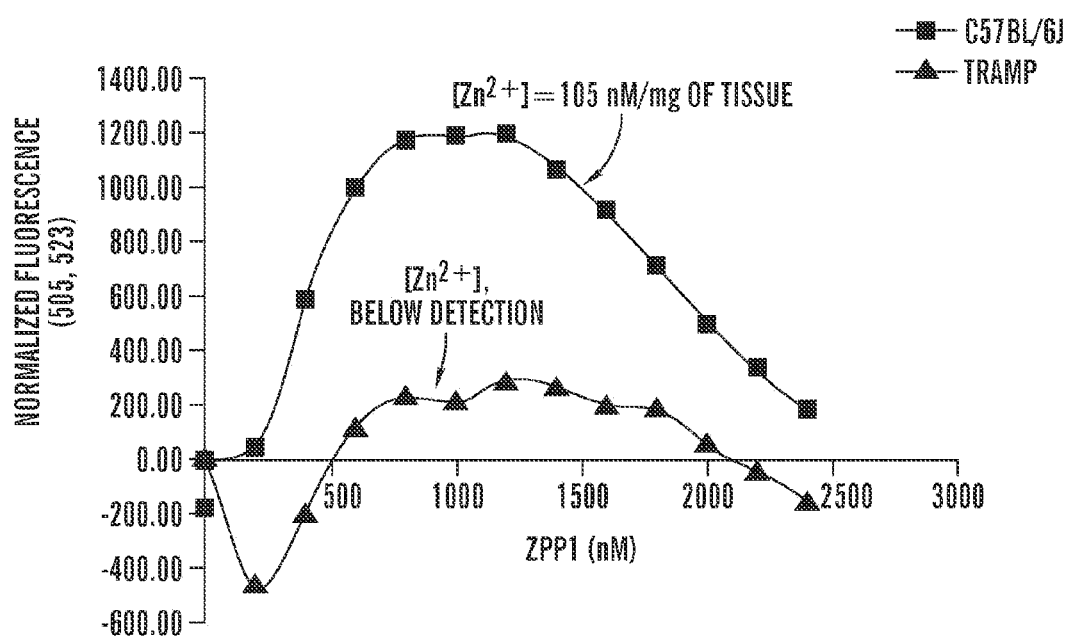
FIG. 8 depicts a chart showing the fluorescence titration of prostatic fluid extracts with a zinc sensor compound for zinc quantification.

Prostatic fluid was extracted from prostates of healthy and prostate tumor-bearing transgenic (TRAMP) mice, followed by fluorescence titration with ZPP1. A clear difference between the levels of zinc in healthy (105 nM/mg of tissue) and tumor-bearing (undetectable) animals was observed, as measured by this approach. See FIG. 8. These findings underscore the diagnostic utility of the method and suggest its immediate clinical applicability for prostate cancer detection. However, the translational potential of this approach is broadly relevant to any disease that demonstrates detectable deviations in labile zinc levels and that can be monitored through analysis of biological fluids or tissue extracts.

Each reference disclosed herein is incorporated by reference herein in its entirety.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. An assay for measuring zinc in a biological sample comprising:
   exposing a biphasic zinc sensor compound to the biological sample obtained from a subject, wherein the zinc sensor compound comprises a fluorophore reporter having two or more recognition units, wherein each of the recognition units is capable of associating with at least one zinc ion, and wherein the zinc sensor compound exhibits a biphasic response to the presence of zinc ions; and
   measuring fluorescence of the fluorophore reporter of the zinc sensor compound after the fluorophore reporter has been exposed to the biological sample,
   wherein a difference in the measurement between the biological sample and a reference is indicative of the subject having or being at risk of a disease associated with a disruption of zinc homeostasis.

2. The assay of claim 1 wherein the fluorophore is 2',7'-dichlorofluorescein or 2',7'-difluorofluorescein.

3. The assay of claim 1 wherein at least one of the two or more recognition units is 1-(pyrazin-2-yl)-N-(pyridin-2-ylmethyl)methanamine.

4. The assay of claim 1 wherein the biphasic zinc sensor compound further comprises at least one spacer.

5. The assay of claim 1 wherein at least one of the recognition units has a structure that is selected from the group consisting of —COO⁻,

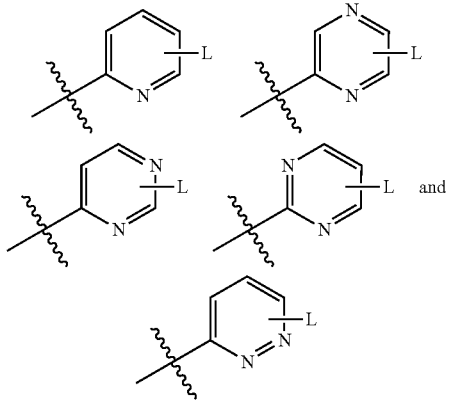

here L is H, $SO_3^-$, or $COO^-$.

6. The assay of claim 1 wherein the biphasic zinc sensor compound is a compound of formula (I):

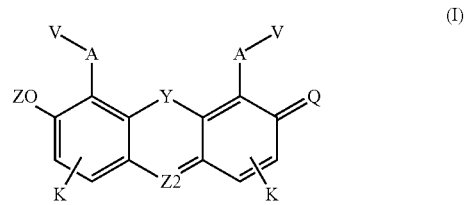

wherein, independently for each occurrence:
K is optionally present and if present, is any one or more of the following substituents at one or more of the substitutable positions of the indicated aromatic ring: alkyl, alkenyl, alkynyl, amino, acyl, acyloxy, acylamino, alkylthio, alkoxyl, carboxyl, nitro, halogen, sulfhydryl, cyano, hydroxyl, carbamoyl and trifluoromethyl;
A is —CH₂—, —C(=O)—, —C(=S)—, —CH₂CH₂—, —CH₂C(=O)—, —CH₂C(=S)— or —C(H)=;
Z is hydrogen or any hydroxyl-protecting group;
Q is O, S or Se;
V is (i) a chemical moiety comprising at least three Lewis basic moieties each independently selected from the group of Lewis basic moieties consisting of: amino, amido, nitro, nitroso, amino alcohol, nitrile, imino, isonitrile, cyanate, isocyanate, phosphate, phosphonate, phosphite, phosphine, phosphine oxide, phosphorothioate, phosphoramidate, phosphonamidite, hydroxyl, carbonyl, aldehyde, ketone, ether, carbamoyl, thiol, sulfide, thiocarbonyl, thioether, mercaptan, sulfonic acid, sulfoxide, sulfate, sulfonate, sulfone, sulfonamide, sulfamoyl, sulfinyl, or heterocyclyl, wherein the at least three Lewis basic moieties are capable of forming a tridentate chelate and at least one of the Lewis basic moieties is heterocyclyl or (ii) an imino group, wherein the imino group is capable of forming a bidentate chelate;

Y is O, S, Se, NR, or C(CH₃)₂, wherein R is an alkyl and R and the methyl groups of C(CH₃)₂ are optionally substituted; and Z2 is N, HOOCCH₂CH₂C—, HOOC—CH═CH—C—, (2-carboxyphenyl)-C—, or (2-sulfophenyl)-C—, wherein for the (2-carboxyphenyl)-C— and (2-sulfophenyl)-C—, the phenyl moiety is optionally substituted with one or more E, wherein for the HOOCCH₂CH₂C— and HOOC—CH═CH—C—, the hydrogen atoms of the —CH₂—'s and —CH═'s moieties are optionally substituted, and wherein E is selected from the group consisting of alkyl, alkenyl, alkynyl, amino, acyl, acyloxy, acylamino, alkylthio, alkoxyl, nitro, halogen, sulfhydryl, cyano, hydroxyl, carbamoyl and trifluoromethyl.

7. The assay of claim 1 wherein the biphasic zinc sensor compound is a compound formula (II):

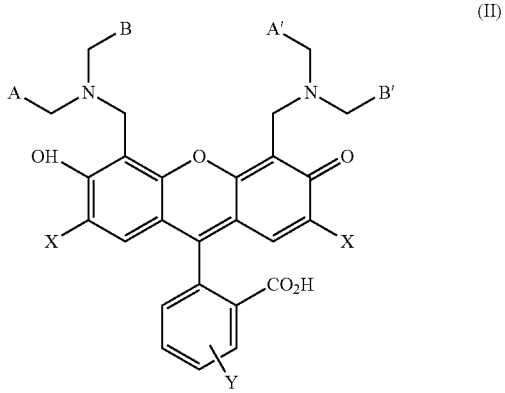

wherein:

A, A', B, and B' are each independently selected from the group consisting of —COO⁻,

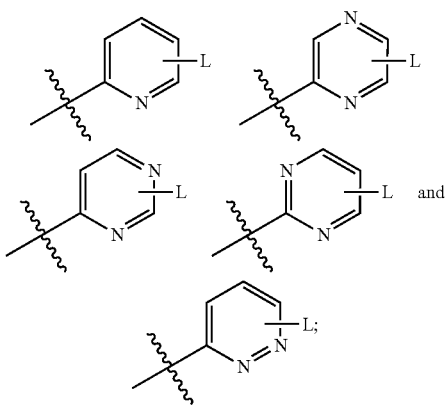

X is H, Cl, or F;
Y is H or —COO⁻; and
L is H, SO₃⁻, or COO⁻.

8. The assay of claim 1 wherein at least one of the recognition units is dipicolylamine or an analog thereof.

9. The assay of claim 1 wherein the fluorophore is more fluorescent when two or more zinc ions are associated with the recognition units than the fluorophore is when no zinc ions are associated with the recognition units or when one zinc ion is associated with the recognition units.

10. The assay of claim 1 wherein the biphasic zinc sensor compound is capable of associating with at least one zinc ion that is mobile in the subject.

11. The assay of claim 10 wherein the zinc ion is intracellular or extracellular.

12. The assay of claim 1 wherein the disease associated with the disruption of zinc homeostasis is prostate cancer.

13. The assay of claim 1, further comprising:
determining a quantity of zinc in the biological sample based on the measurement or measurements.

14. The assay of claim 1 wherein the exposure is titration of the biological sample with the biphasic zinc sensor compound.

15. The assay of claim 12 wherein the biological sample is a prostate fluid extract and the prostate fluid extract is obtained from an ejaculate, a seminal fluid, a prostatic fluid, a biopsy sample, or a combination thereof.

16. The assay of claim 15 wherein at least one of the measurements is measured fluorescence and the measurement is indicative that the human has a normal prostate, that the human has a prostate that is free of cancer, that the human has prostate cancer, or that the human has benign prostatic hyperplasia.

17. The assay of claim 16 wherein the at least one of the measurements is normalized to a volume of the patient's prostate and to serum zinc concentration in the patient.

18. The assay of claim 10, wherein the subject is a mammal.

19. The assay of claim 18, wherein the mammal is a human.

20. The assay of claim 14, wherein the quantity of zinc is determined from a concentration of the zinc sensor compound giving a maximum optical response during the titration.

21. The assay of claim 1, wherein the biphasic zinc sensor compound is a compound of formula (III) or an analog thereof, wherein the formula (III) has a structure:

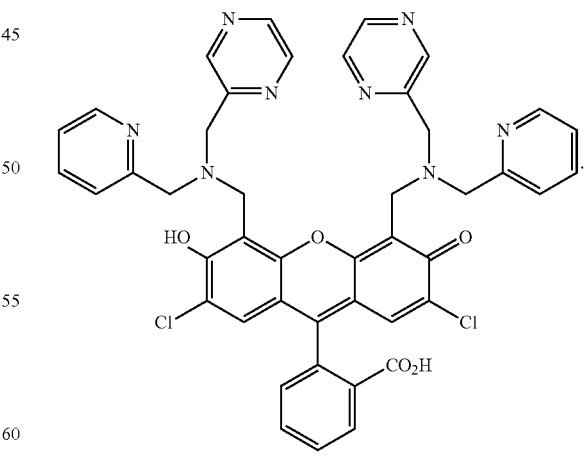

* * * * *